United States Patent [19]

Kyo et al.

[11] 4,069,261

[45] Jan. 17, 1978

[54] PROCESS FOR THE PRODUCTION OF POLYHYDRIC ALCOHOLS

[75] Inventors: Sunao Kyo; Katsuhiko Hayashi; Hidetsugu Tanaka; Hideaki Oka, all of Ibaragi, Japan

[73] Assignee: Kuraray Co., Ltd., Kurashiki, Japan

[21] Appl. No.: 609,722

[22] Filed: Sept. 2, 1975

Related U.S. Application Data

[63] Continuation of Ser. No. 420,849, Dec. 3, 1973, abandoned.

[30] Foreign Application Priority Data

Dec. 2, 1972 Japan .................................. 47-120964

[51] Int. Cl.² ............................................. C07C 29/00
[52] U.S. Cl. ............................ 260/635 E; 260/462 R; 260/617 R; 260/618 R
[58] Field of Search ............ 260/635 E, 617 R, 618 R

[56] References Cited

U.S. PATENT DOCUMENTS

| 2,122,813 | 7/1938 | Groll et al. ........................ 260/635 E |
| 2,307,894 | 1/1943 | Mikeska ............................ 260/635 E |
| 2,366,497 | 1/1945 | Dawson ................................ 260/682 |
| 2,885,445 | 5/1959 | Sharp et al. ...................... 260/643 A |
| 3,475,499 | 10/1969 | Winnick ............................ 260/635 E |

OTHER PUBLICATIONS

Ryss, "The Chemistry of Fluorine and its Inorganic Compounds," Translation from Russian, (1960), pp. 545, 546, 555, 556.

*Primary Examiner*—Joseph E. Evans
*Attorney, Agent, or Firm*—Bacon & Thomas

[57] ABSTRACT

Polyhydric alcohols can be produced in high selectivity from substituted 1,3-dioxanes containing at least one hydroxyalkyl group by heating, in the presence of water, said 1,3-dioxane or mixtures thereof in contact with boric acid, boric acid anhydride or a boron-containing compound capable of forming boric acid under the reaction conditions and recovering the polyhydric alcohols corresponding to said 1,3-dioxanes.

7 Claims, No Drawings

PROCESS FOR THE PRODUCTION OF POLYHYDRIC ALCOHOLS

This is a continuation of application Ser. No. 420,849, filed Dec. 3, 1973, now abandoned.

BACKGROUND OF THE INVENTION

1. Field of the Invention

This invention relates to a process for the production of polyhydric alcohols from 1,3-dioxanes containing at least one hydroxyl group, and more particularly, to a process for the production of polyhydric alcohols containing ($n$ + 2) hydroxyl groups from substituted 1,3-dioxanes containing ($n$) hydroxyl groups, wherein $n$ is an integer of at least 1.

2. Description of the Prior Art

Heretofore, the most prevalent method of obtaining polyhydric alcohols by the cleavage of the 1,3-dioxane ring has been the solvolysis reaction which is conducted in the presence of a strong acid. Said reaction may be expressed by the following equation:

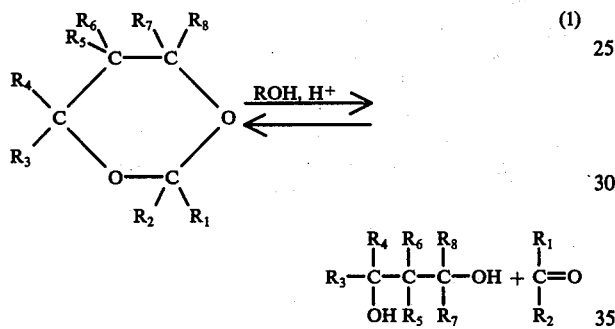

In the above equation, R represents H or a lower alkyl group, and $R_1$ to $R_8$ represent any of H, a lower alkyl group, a cycloalkyl group and an aryl group wherein at least one of $R_1$ to $R_8$ is a hydroxyalkyl group.

As is seen from the above equation (1), the solvolysis reaction attains equilibrium and hence the formed carbonyl compound should be eliminated from the reaction system to promote the reaction. Elimination of a carbonyl compound can usually be achieved by conducting the alcolysis reaction in a lower alcohol whereby the formed carbonyl compound is converted to the corresponding low boiling acetal compound which can be easily removed from the reaction system. In this case, however, undesirable side-reactions occur. A considerable amount of ethers are formed through the dehydrolysis reaction between the alcohol as a solvent and the formed polyhydric alcohol and unsaturated alcohols and cyclic ethers are formed through the intramolecular dehydrolysis of the formed polyhydric alcohol in addition to the inevitable dehydrolysis reaction of the alcohol by itself as a solvent. Therefore, the above-mentioned reaction has been found uneconomical for obtaining polyhydric alcohols.

The formation of the by-products as above indicated depends upon the structure of the starting substituted 1,3-dioxane. In general, the more the number of substituents at the 4th and 6th positions on 1,3-dioxane ring is, the more remarkable the occurrence of the side reactions is. In other words, if each of $R_3$, $R_4$, $R_7$ and $R_8$ in the above formula is a substituent such as an alkyl group, the yield of the intended polyhydric alcohol is extremely lowered. For example, Zhur. Obshchei Khim. 26, 2749-2754 (1956) discloses that methanolysis of 4-methyl-1,3-dioxane in the presence of a sulfuric acid catalyst provides the corresponding glycol in a yield of 82% but methanolysis of 4,4-dimethyland 2,4,4,6-tetramethyl-1,3-dioxane gives the corresponding glycols in yields of only 38.7% and 18.2%, respectively.

When the above reaction is carried out in the presence of water, that is to say hydrolysis, the yield of polyhydric alcohols is very low resulting in no practical application because the reaction rate is low and the formed carbonyl compound is difficult to remove from the reaction system. Where the reaction temperature and/or concentration of catalyst is increased in order to increase the reaction rate, successive side-reactions also occur vigorously so that desirable results cannot be obtained. For instance, in the hydrolysis reaction of 4-hydroxyethyl-4-methyl-1,3-dioxane in the presence of a sulfuric acid catalyst at a temperature of 100° – 110° C., conducted by blowing steam into the reactor to eliminate the formed formaldehyde, dihydropyran is formed as the main product by the successive reactions and is steam distilled and recovered as shown by the following equations.

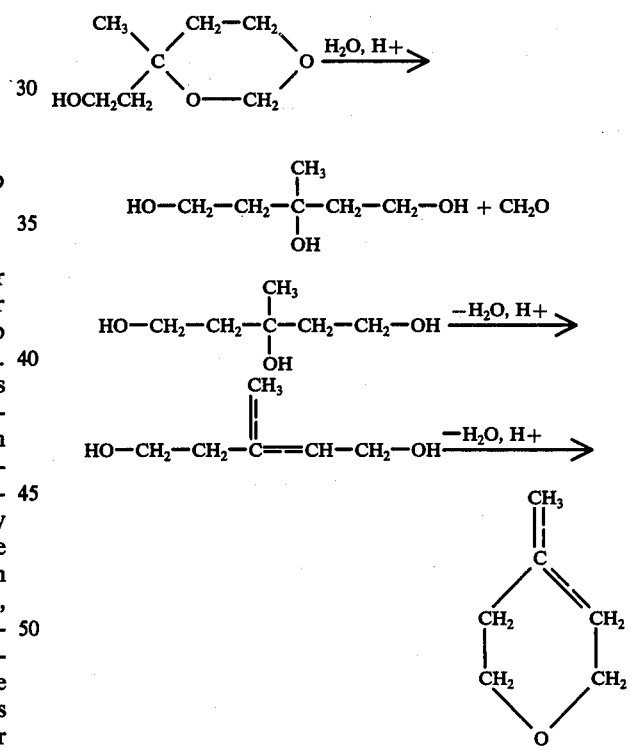

Thus, according to the prior art, the production of polyhydric alcohols by the cleavage of the 1,3-dioxane ring is economically unsuccessful. Furthermore, the prior art processes which teach the use of organic or inorganic strong acids such as sulfuric and sulfonic acids as a catalyst are also unsuited for industrial operation since equipment corrosion results. In addition, organic carboxylic acids such as acetic acid cannot be used as a catalyst for the production of the corresponding polyhydric alcohols from 1,3-dioxanes, because organic carboxylic acids have weak acidity and hence do not easily promote the cleavage of the dioxane ring.

SUMMARY OF THE INVENTION

The object of the present invention is, therefore, to provide a process for producing polyhydric alcohols from the corresponding substituted 1,3-dioxanes without the above difficulties.

It has now been found, according to the present invention, that polyhydric alcohols can be selectively produced by heating, in the presence of water, a mixture of a substituted 1,3-dioxane (or mixtures thereof) containing at least one hydroxyalkyl group in the molecule and boric acid, boric acid anhydride or a boron-containing compound capable of forming boric acid under the reaction conditions.

DESCRIPTION OF THE PREFERRED EMBODIMENTS

As is well known, the acidity of boric acid is too weak to be subjected to conventional neutralization titration in aqueous solution (pKa 9.14 at 20° C.). The neutralization titration of boric acid becomes possible by forming a complex compound with mannitol or other $C_6$-monosaccharides to increase the acidity. However, said complex compound has much the same acidity as acetic acid (pKa 4.76). Therefore, it is unexpected that boric acid has such a surprising action upon the substituted 1,3-dioxane as above mentioned according to the present invention.

One of the advantages of the invention is that the successive side-reactions hardly occur and that the selectivity of the polyhydric alcohol is extremely high.

Although preferred embodiments will be described below, the broad invention is not limited to any particular starting material (i.e., the 1,3-dioxane compound). Any substituted 1,3-dioxane can be employed as long as one of the substituents is a hydroxyalkyl group. Similarly, the broad invention is not limited to a particular temperature range, reaction ratios, pressures, amounts of water, etc. Broadly stated, the invention is in the use of the boron compound (e.g., boric acid) to selectively produce polyhydric alcohols from the corresponding substituted 1,3-dioxanes.

In the present invention, preferred embodiments of the substituted 1,3-dioxanes containing at least one hydroxyalkyl group (hereinafter referred to as "dioxane alcohols") to be used for the production of the corresponding polyhydric alcohols are 4-(β-hydroxyethyl)-4-methyl-1,3-dioxane, 4,4-dimethyl-5-hydroxymethyl-1,3-dioxane, and 5-(2-hydroxypropane-2-yl)-1,3-dioxane.

The amount of boric acid, boric acid anhydride and boron-containing compound capable of forming boric acid under the reaction conditions is not particularly limited in the present invention. However, it is recommended that said compound be used in an amount of from 0.5 to 2.5 times, by mole based on boric acid, the amount of the dioxane alcohol in view of the reaction rate and reaction operation. However, any amount may be used depending on the results desired.

The boron-containing compound capable of forming boric acid under the reaction conditions includes, for example, metaboric acid, hypoboric acid, tetraboric acid, and their esters and boric acid esters. As for the hypoboric acid esters and boric acid esters, those obtained by using the starting dioxane alcohols or the polyhydric alcohols corresponding to the dioxane alcohols are particularly preferred from the point of view that the reaction product according to the invention substantially consists of one kind of carbonyl compound and one kind of polyhydric alcohol resulting in easy recovery and purifcation of the product. However, any boron-containing compound capable of forming boric acid under the conditions of reaction is operable in the present invention.

In the present invention, when the reaction temperature is below 90° C., reaction rate decreases. On the other hand, a reaction temperature of about 180° C. sometimes brings about an undesirable stain in the reaction mixture. Accordingly, a reaction temperature of 90° C. to 180° C., particularly 105° to 150° C. is preferable, although higher and lower temperatures can be employed depending on the desired results.

The water which must be present in the reaction system may be added to the system at the beginning of or during the course of the reaction. Various techniques of adding water to the reaction system can be employed. For example, a predetermined amount of water in the form of liquid can be added to the system at the beginning of the reaction. Alternatively, water in the form of steam may be blown into the system to contact the reaction mixture accompanied by distilling off water together with the formed carbonyl compound. The latter method is preferred from the point of view of acceleration of the reaction and easy recovery of the formed carbonyl compound although those skilled in the art will realize that the particular technique chosen for adding the water is not critical. Water is generally used in an amount ranging from 0.2 to 100 times by weight based on the weight of the starting dioxane alcohols.

The time of reaction is not critical and, generally, the reaction is conducted until the desired conversion is attained from an economical standpoint.

After the reaction, boric acid can be mostly precipitated by cooling the reaction mixture and may be recovered by filtration. Therefore, the net reaction according to the present invention can be regarded as a hydrolysis reaction represented by the following equation:

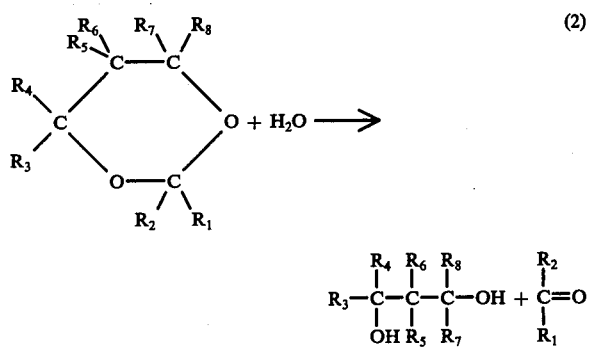

In the formula, $R_1$ to $R_8$ can be any substituent as long as at least one of $R_1$ to $R_8$ is a hydroxyalkyl group of 1 to 4 carbon atoms. For instance, at least one of $R_1$ to $R_8$ is a hydroxyalkyl group and the others may be a hydrogen atom, an alkyl group having 1 to 6 carbon atoms, a cycloalkyl group (of 5 to 9 carbon atoms) or an aryl group of 5 to 8 carbon atoms. It is most preferred to use those dioxane alcohols where at least one of $R_1$ to $R_8$ is a hydroxyalkyl group having 1 to 4 carbon atoms and the others of $R_1$ to $R_8$ are hydrogen atoms and/or alkyl groups having 1 to 4 carbon atoms, which are easily obtainable.

Typical examples of the aryl group and cycloalkyl groups are phenyl, tolyl, cyclohexyl, and methylcyclohexyl group derived from α-methylstyrene, isopropenylcyclohexane, and their methyl derivatives.

The polyhydric alcohols obtained by the method of the present invention are useful for various applications such as additives for synthetic polymers, plasticizers, humectants and intermediates for chemical synthesis.

Presently preferred and practical embodiments of the present invention are illustratively shown in the following examples, which are not intended to be limiting in nature.

EXAMPLE 1

73 g (0.5 mole) of 4-(β-hydroxyethyl)-4-methyl-1,3-dioxane and 0.75 mole of boric acid were charged to a 200 ml three necked flask equipped with a fractional distillation column (length=20 cm) having a Liebig condenser connected therewith, a thermometer and a inlet pipe for water steam. 800 g of steam from a steam generator has blown into the reaction mixture for 3 hours while maintaining the contents at a temperature of 120° C. ± 5° C. The formaldehyde content in the distilled water was determined by the conventional sodium sulfite method.

After the reaction, the reaction mixture was diluted with 100 ml of water and was cooled to precipitate boric acid which was then filtered out. The remaining boric acid was separated by conventional techniques (i.e., the formation of hardly soluble salts or low boiling esters). Formaldehyde was titrated by the sodium sulphite method. The unreacted starting material and formed 3-methyl-1,3,5-pentanetriol contents were determined by means of gas-liquid chromatography. The results were as follows:

| | |
|---|---|
| Conversion | 78.2% |
| Selectivity of 3-methyl-pentane-1,3,5-triol | 97.5% |
| Selectivity of formaldehyde | 99.4% |

EXAMPLE 2

Example 1 was repeated except that 73 g (0.5 mole) of 4,4-dimethyl-5-hydroxymethyl-1,3-dioxane was used in place of 4-(β-hydroxyethyl)-4-methyl-1,3-dioxane. The results were as follows:

| | |
|---|---|
| Conversion | 55.8% |
| Selectivity of product 2-(2-hydroxypropane-2-yl)-propane-1,3-diol | 99.0% |
| Selectivity of formaldehyde | 97.1% |

EXAMPLE 3

To a 300 ml two-necked flask, 73 g (0.5 mole) of 4-(β-hydroxyethyl)-4-methyl-1,3-dioxane, 46.5 g (0.75 mole) of boric acid and 100 ml of water were charged and the mixture was heated to reflux for 5 hours. The contents were kept at a temperature of 104° to 105° C. during the reaction.

The reaction mixture was filtered after cooling and the filtrate was subjected to gas-liquid chromatographic analysis Organic material other than 37 g of unreacted starting material, 33 g of 3-methylpentane-1,3,5-triol and 7.4 g of formaldehyde was hardly observed in the reaction liquid. The above values correspond to the stoichiometric yields relative to the reacted starting material.

EXAMPLE 4

1 kg of the mixture of (I) 4-(β-hydroxyethyl)-4-methyl-1,3-dioxane and (II) 4,4-dimethyl-5-hydroxymethyl-1,3-dioxane (85 : 15 weight ratio), 500 g of boric acid and 300 g of water were charged to a 2l three-necked flask equipped with a stirrer, a thermometer and an inlet for steam, and dissolved with agitation at 110° C.

Then, the stirrer was replaced by a McMahon packed column, a 7 kg of steam was blown into the reactor for 8 hours. The contents were kept at a temperature of 125° - 130° C. during the reaction. Steam coming through the reaction mixture was condensed by a condenser and was subjected to a determination of its formaldehyde content. The reaction mixture was diluted with 1 kg of water and was cooled to precipitate boric acid which was then filtered out. The filtrate was subjected to gas-liquid chromatographic analysis. The organic materials dissolved in the filtrate were as follows:

| | |
|---|---|
| Unreacted starting material (I : II = 38 : 62 weight ratio) | 127 g |
| 3-methyl-pentane-1,3,5-triol | 736 g |
| 2-(2-hydroxypropane-2-yl)-propane-1,3-diol | 56 g |
| Formaldehyde | 179 g |

EXAMPLE 5

31 g of boric acid was added to 200 g of 3-methyl-pentane-1,3,5-triol and the mixture was dissolved with heat. Then, the excessive triol was removed by vacuum distillation to give the boric acid ester of said triol remaining undistilled at the bottom. Said ester was a glassy substance solid state and had the composition of 2 moles of said triol condensed with 1 mole of boric acid.

To the boric ester, 73 g of 4-(β-hydroxyethyl)-4-methyl-1,3-dioxane was added and the reaction was carried out in the same manner as in Example 1. The results were as follows: conversion 53.0%, selectivities of 3-methyl-pentane-1,3,5-triol and formaldehyde were both 98.2%.

EXAMPLE 6

Example 1 repeated except that 133 g (0.5 mole) of 3-methyl-3-butenylborate [$(C_5H_9O)_3B$, boiling point: 98° - 103° C/1.3 mm Hg] was used in place of boric acid. 3-methyl-3-butenylborate was hydrolyzed at the initial stage of the reaction and 3-methyl-3-butenol-1 was distilled off together with water.

As the results of subjecting the reaction mixture to gas chromatographic analysis, conversion of 4-(β-hydroxyethyl)-4-methyl-1,3-dioxane was 71.7% and the selectivities of 3-methylpentane-1,3,5-triol and formaldehyde were 96.2% and 97.5%, respectively.

While the invention has been described with reference to preferred embodiments thereof, those skilled in the art will realize that various changes, modifications and substitutions may be made therein without departing from the spirit and scope of the invention. It is the intention, therefore, that the invention be limited only by the appended claims.

What is claimed is:

1. Process for the production of polyhydric alcohols from a substituted 1,3-dioxane containing at least one hydroxy alkyl group in the molecule which comprises heating said 1,3-dioxane or mixtures thereof in contact with boric acid anhydride or a boric acid compound selected from the group consisting of boric acid, metaboric acid, hypoboric acid, tetraboric acid and their esters at a temperature of from about 90° C. to 180° C., blowing water in the form of steam into the reaction system and recovering said polyhydric alcohol.

2. The process of claim 1, wherein said 1,3-dioxanes have the following formula:

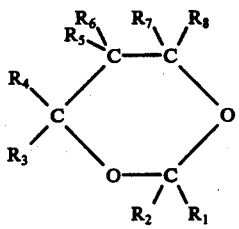

wherein at least one of $R_1$ to $R_8$ is a hydroxyalkyl group of 1 to 4 carbon atoms and the others of said $R_1$ to $R_8$ are selected from the group consisting of a hydrogen atom, an alkyl group having 1 to 6 carbon atoms, a cycloalkyl group of 5 to 9 carbon atoms and an aryl group of 6 to 8 carbon atoms.

3. The process of claim 1, wherein said boric acid ester is prepared by the reaction of one of the said boric acid compounds and a member selected from the group consisting of said substituted 1,3-dioxane, said polyhydric alcohols and 3-methyl-3-butene-1-ol.

4. The process of claim 1, wherein said member is used in an amount of 0.5 to 2.5 times, by mole, based on boric acid, the amount of said 1,3-dioxane.

5. The process of claim 1, wherein said hydroxyalkyl group has from 1 to 4 carbon atoms and the others of said $R_1$ to $R_8$ are selected from the group consisting of a hydrogen atom, an alkyl group of 1 to 4 carbon atoms and mixtures thereof.

6. The process of claim 1, wherein said substituted 1,3-dioxane is 4-(β-hydroxyethyl)-4-methyl-1,3-dioxane; 4,4-dimethyl-5-hydroxymethyl-1,3-dioxane, or 5-(2-hydroxypropane-2-yl)-1,3-dioxane.

7. The process of claim 1, wherein water is present in an amount of from 0.2 to 100 times, by weight, the amount of said 1,3-dioxane.

* * * * *

UNITED STATES PATENT OFFICE
CERTIFICATE OF CORRECTION

Patent No. 4,069,261  Dated January 17, 1978

Inventor(s) Sunao KYO; Katsuhiko HAYASHI; Hidetsugu TANAKA; and Hideaki OKA

It is certified that error appears in the above-identified patent and that said Letters Patent are hereby corrected as shown below:

Column 2, line 4, "4,4-dimethyland" should read -- 4,4-dimethyl-and --;

Column 2, lines 26-55, "H+" should read -- $H^+$ --;

Column 6, line 37, "glassy substance solid state" should read -- glassy substance near solid state --.

Signed and Sealed this

Sixth Day of March 1979

[SEAL]

Attest:

RUTH C. MASON
*Attesting Officer*

DONALD W. BANNER
*Commissioner of Patents and Trademarks*